United States Patent
Kim

(10) Patent No.: US 10,830,776 B2
(45) Date of Patent: *Nov. 10, 2020

(54) FUNCTIONALIZED EYEWEAR DEVICE FOR DETECTING BIOMARKER IN TEARS

(71) Applicant: University of Central Florida Research Foundation, Inc., Orlando, FL (US)

(72) Inventor: Yoon-Seong Kim, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/430,183

(22) Filed: Jun. 3, 2019

(65) Prior Publication Data

US 2019/0383833 A1    Dec. 19, 2019

Related U.S. Application Data

(63) Continuation of application No. 15/505,373, filed as application No. PCT/US2015/046344 on Aug. 21, 2015, now Pat. No. 10,309,975.

(60) Provisional application No. 62/040,085, filed on Aug. 21, 2014.

(51) Int. Cl.

| | | |
|---|---|---|
| *C07H 21/04* | (2006.01) | |
| *G01N 33/68* | (2006.01) | |
| *C08B 37/08* | (2006.01) | |
| *C08L 5/08* | (2006.01) | |
| *G02C 7/04* | (2006.01) | |
| *G01N 33/52* | (2006.01) | |

(52) U.S. Cl.
CPC ..... *G01N 33/6896* (2013.01); *C08B 37/0072* (2013.01); *C08L 5/08* (2013.01); *G01N 33/528* (2013.01); *G02C 7/04* (2013.01); *G01N 2333/47* (2013.01); *G01N 2800/2821* (2013.01)

(58) Field of Classification Search
None
See application file for complete search history.

(56) References Cited

U.S. PATENT DOCUMENTS

| | | |
|---|---|---|
| 2004/0110276 A1 | 6/2004 | Amontov et al. |
| 2004/0181172 A1 | 9/2004 | Carney et al. |
| 2006/0068416 A1 | 3/2006 | Schluesener |
| 2010/0105098 A1 | 4/2010 | Frederiske et al. |
| 2013/0022538 A1 | 1/2013 | Rossi et al. |
| 2013/0338039 A1 | 12/2013 | Mazed et al. |
| 2014/0088381 A1 | 3/2014 | Etzkorn et al. |

FOREIGN PATENT DOCUMENTS

| | | |
|---|---|---|
| DE | 102010038842 | 2/2012 |
| EP | 2316935 | 5/2011 |
| WO | 2004080297 | 9/2004 |

OTHER PUBLICATIONS

International Search Report and Written Opinion for PCT Application PCT/US15/046344 dated Feb. 2, 2016, pp. 1-15.
Li et al., "Endonuclease-responsive aptamer-functionalized hydrogel coating for sequential catch and release of cancer cells", Biomaterials, 2013, vol. 34, pp. 460-469.
Tsukakoshi et al., "Screening of DNA aptamer which binds to x-synuclein", Biotechnol Lett, 2010, vol. 32, pp 643-648.
Farrar, Christian T. et al., "RNA Aptamer Probes as Optical Imaging Agents for the Detection of Amyloid Plaques", PLOS One, Feb. 2014, vol. 9, Issue 2, e89901, 8 pages.
Lee, Jung Hoon et al., "Facilitated Tau Degradation by USP14 Aptamers via Enhanced Proteasome Activity", Scientific Reports Jun. 2015, 5:10757, DOI: 10.1038/srep10757, 11 pages.
Sarrell, Claire J. et al., "Distinguishing Closely Related Amyloid Precursors Using an RNA Aptamer", J Biol Chem. Sep. 2014, vol. 289, Issue 39, pp. 26859-26871.
Krylova, Svetlana M. et al., "Tau protein binds single-stranded DNA sequence specifically—the proof obtained in vitro with non-equilibrium capillary electrophoresis of equilibrium mixtures", FEBS Letters, 2005, vol. 579, Issue 6, pp. 1371-1375.
Rahimi, Farid et al., "Selection of Aptamers for Amyloid B-Protein, the Causative Agent of Alzheimer's Disease", J Vis Exp. 2010, http://www.jove.com/details.php?id=1955, 7 pages.
Want, Xu et al., "The novel amyloid-beta peptide aptamer inhibits intracellular amyloid-beta peptide toxicity", Neural Regeneration Research, 2013, vol. 8, Issue 1, pp. 39-48.
Takahashi, Tsuyoshi et al., "RNA aptamers selected against amyloid B-peptide (AB) inhibit the aggregation of AB" j, Molecular Biosystems, 2009 vol. 5, Issue 9, pp. 986-991.

*Primary Examiner* — Kimberly Chong
(74) *Attorney, Agent, or Firm* — Timothy H. Van Dyke; Wolter Van Dyke Davis, PLLC

(57) ABSTRACT

Disclosed herein is a functionalized eyewear device that is adapted for collecting and analyzing disease biomarkers. Specifically, exemplified is a contact lens that has aptamer molecules associated therewith for binding to a specific biomarker (or biomarkers). The eyewear device is useful for detecting and diagnosing medical conditions.

11 Claims, 2 Drawing Sheets

Specification includes a Sequence Listing.

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gcctgtggtg ttggggcggg tgcg                                          24
```

FUNCTIONALIZED EYEWEAR DEVICE FOR DETECTING BIOMARKER IN TEARS

BACKGROUND

There is an urgent need to establish noninvasive biomarkers which enable early detection of a range of diseases such as cancers and neurodegenerative disorders. Recent advances in the field of "omics" have facilitated identification of novel biomarkers from various biospecimens. This is well reflected in the recent global biomarkers market research anticipating growth from $29.3 billion in 2013 to $53.6 billion in 2018, a CAGR of 12.8% (by PRNewswire).

Recent studies have demonstrated that the tear fluid is a unique biospecimen containing mucins, lipids, more than 500 proteins, peptides, cytokines and neurotransmitters. In particular, the scarcity of albumin and immunoglobulins in tears while abundant in serum makes analysis straightforward. Changes in composition of tears have been reported in various conditions including not only local eye diseases but systemic conditions such as cancers and diabetes. The dynamic changes in composition of tears in response to systemic pathophysiologic conditions render tears as an alternative source of biomarkers.

The tear film is a kind of hydrated mucin gel containing fluid, electrolytes, proteins and other aqueous components secreted by lacrimal glands and ocular surface epitheoium, and it is covered by a lipid layer generated by meibomian glands. Tear fluids have been used to assess stress levels in individuals, specific markers such as serotonin, cortisol and DHEA levels are indicative of stress levels. Various techniques such as Gas chromatography-mass spectrometry (GC-MS), Liquid chromatography-mass spectrometry (LC-MS), Immunoassays for steroid hormones have been used to measure levels of specific markers.

DETAILED DESCRIPTION

Figure 1:
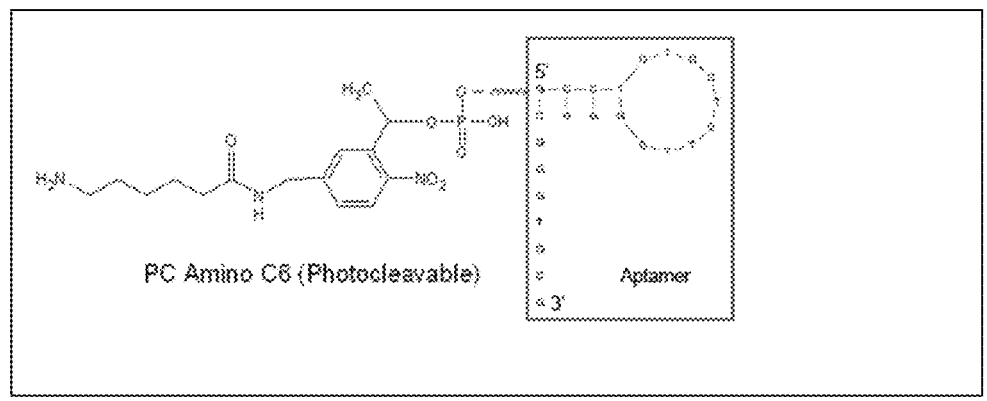
FIG. 1 shows an example of an aptamer modified for binding to a contact lens surface.

Despite its non-invasive nature of collection, limited amount of tear fluid compared to other biospecimens such as blood, urine and saliva, tears require a more convenient, standardized method for collection along with reliable and reproducible techniques for analysis. Recently, contact lenses have been used for various purposes other than vision correction or cosmetics. However, it has been realized that the use of eyewear devices for other medical purposes, such as interacting with tear fluid are underdeveloped.

One aspect of what is disclosed herein pertains to eyewear devices that include molecules associated therewith that can interact with biomarkers present in tears. In one embodiment, disclosed is a contact lens that has a functionalized surface to enable detection of certain biomarkers. In a more specific embodiment, the contact lens has an aptamer associated therewith for detecting such biomarker.

Compared to the one-time collection of tears, contact lens enables cumulative detection of biomarker during wearing period and potentially increase sensitivity of the assay. Multiplexing to detect various biomarkers at the same time (i.e. via one eyewear device) is achievable due to the large surface area of contact lens (Contact lens biomarkers chip). According to a certain embodiment, disclosed is an eyewear device for detecting at least two different biomarker molecules on eye or in tear fluid, wherein the device is configured to rest on the eye and comprising at least two different biomarker-capture molecules associated therewith.

The term "biocapture molecule" refers to a molecule associated with an eyewear device that binds to a target molecule on the eye or present in tear fluid. Specific examples of biocapture molecules include antibodies or aptamers.

The term "aptamer" as used herein pertains to an oligonucleic acid or peptide molecule that binds to a specific target molecule. When the aptamer includes an oligonucleic acid the oligonucleic acid may be single or double stranded and may have a fold or other conformation where part of the aptamer associates with another part of the aptamer.

Biomarkers that may be targeted by a biocapture molecule associated with an eyewear device may include, but are not limited to, those associated with Neurodegenerative diseases (e.g. Parkinson's disease, Alzheimer's disease) such as alpha-synuclein, Amyloid Beta, Tau protein, Insulin Degrading Enzyme and amyloid precursor protein. Other biomarkers may include those associated with dry eye such as alpha-1-antitrypsin, calgranulin A, calgranulin B, S100 A4, lactoferrin and lysozyme. Another biomarker may include biomarkers for various cancers, such as but not limited to, prostate specific antigen, or c-erB-2, VEGF, EGF, and CeA. Other biomarkers may include homocysteine, haemoglobin A1c, glucose, or thyroid hormones. Further still, other biomarkers may include neurotransmitters and small molecules (dopamine, serotonin, homocysteine etc), inflammatory cytokines (TNF-alpha, IL-1 beta, IL-6, IL-8, IL-12, IFN-gamma, etc), noncytokine proteins (lysozyme, lactoglobin, EGF, lipocalin-1, cystatin S100, alpha1-antitrypsin, alpha-enolase, calgranulin A and B, prolactin inducible protein), MCP-1, lipocalin-1, heat shock protein (HSPs), complement proteins. In a certain embodiment, the biomarker is alpha-1 antichymotrypsin (serpin A3) which has been shown to be elevated in tears of patients with multiple sclerosis. Salvisberg, C, *Proteomics Clin Appl.* 2014 April; 8 (3-4): 185-94. In another certain embodiment, the biomarker is directed to TNF-Alpha, which is known to be elevated in diabetic retinopathy and malignant disease.

Examples of specific aptamers known in the art for various biomarkers include, but are not limited to, those described in the following:

1. Rahimi, J Vis Exp, 2010 13(39):1955 (amyloid beta)
2. Wang X, Yang Y, Jia M, et al. The novel amyloid-beta peptide aptamer inhibits intracellular amyloid-beta peptide toxicity. Neural Regeneration Research. 2013; 8(1): 39-48. doi:10.3969/j.issn.1673-5374.2013.01.005.
3. Takahashi et al., Mol Biosyst. 2009 September; 5(9):986-91 (amyloid beta)
4. Tsukakoshi et al, Biotechnol Lett. 2010 May; 32(5):643-8 (alpha synuclein)
5. Krylova et al., Febs Letters, 2005, Volume 579, Issue 6, Pages 1371-1375 (tau)
6. DE 102010038842 A1 (tau)
7. Farrar C T, William C M, Hudry E, Hashimoto T, Hyman B T (2014) RNA Aptamer Probes as Optical Imaging Agents for the Detection of Amyloid Plaques. PLoS ONE 9(2): e89901
8. Lee et al., Scientific Reports (Impact Factor: 5.58). 06/2015; 5:10757 (tau)

9. Sarell et al., J Biol Chem. 2014 Sep. 26; 289(39):26859-71 (Amyloid precursor protein)
10. US Pat Pub 20130022538 alpha-1-antitrypsin
11. EP 2316935 A1 (IL-7)

According to another embodiment, disclosed is a method of making a functionalized eyewear device for detecting a molecule on eye or tear fluid. The method includes attaching an aptamer to a surface of the device. The device may be made of a material that provides an available hydroxyl group (or carboxylic acid, aromatic amine, amide, hydralizide, aldehyde, thiol, or epoxy) for attachment of said aptamer. The method may further include silanizing the hydroxyl group. Silanizing the hydroxyl group may involve subjecting the hydroxyl group or other noted group to at least one silane compound. Examples of silane compounds include but are not limited to, 3-glycidoxypropyltrimethoxysilane (3-GPTMS), 3-mercaptopropyltrimetoxysilane or 3-aminopropyltrimetoxysilane. The method may also involve providing an aptamer that includes a hydrocarbon chain having a terminus with a functional group that interacts with a terminus of the silane compound.

In certain embodiments, a number of chemical reactions could be used: one end of the aptamer (either 5'- or 3'-end) can be easily modified by attaching functional groups such as an amine or carboxy (For peptide based aptamers, these can be modified for attachment or the native amino or carboxyl termini can be involved for attachment). Then this functional group can be further linked to materials of the contact lens such as HEMA (2-hydroxy ethyl methacrylate), silicone hydrogel, methacrylic acid, polyvinyl alcohol (PVA) or N-vinyl pyrrolidone (NVP), polyHEMA or methyl methacrylate (MMA), polyethylene glycol, N,N-dimethylacrylamide, N-carboxyl vinyl ester, or plasma oxidized surface via an interactive group such as a hydroxyl that is exposed on the surface as discussed above. In a further more specific embodiment, a linker can be attached to the surface of contact lens that is then bound to a group on functional group associated with the aptamer.

According to another embodiment, disclosed is a method of detecting a biomarker in tear fluid. The method may involve applying to an eye of a subject a functionalized eyewear device that includes a biomarker-capture molecule associated therewith for a period of time for a biomarker to bind with said biomarker-capture molecule to produce a sample-loaded device; and subjecting the sample-loaded device to a detection process. The detection process may involve subjecting the sample-loaded device with chemical reagents that produce a detectable signal, such as a colorimetric detectable signal. A colorimetric detectable signal includes, but is not limited to, fluorescence, luminescence, chemiluminescence, or a color formation, or changes in any of the foregoing, including changes in intensity, duration, anisotropy or polarization, or color change.

In a further embodiment, disclosed is a method of determining a disease state that involves applying to an eye of a subject a functionalized eyewear device that includes a biomarker-capture molecule associated therewith for a period of time for a biomarker indicative of the disease state to bind with said biomarker-capture molecule to produce a sample-loaded device; subjecting said sample-loaded device to a detection process; and determining the disease state based on presence or amount of said biomarker. The disease state may pertain to, but is not limited to, a neurological condition, cancer, diabetes, eye disease, or inflammation.

EXAMPLES

Figure 2:
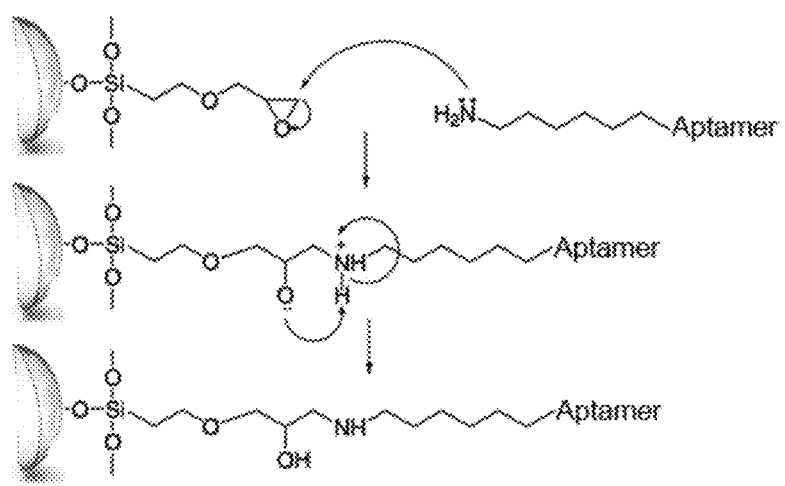
FIG. 2 is a diagram showing binding of a modified aptamer to contact lens surface.

Example 1: Surface Functionalization with Aptamer for Human Alpha-Synuclein Oligomer 1. Contact Lens: Claren Ultra-Soo Lens (Interojo Inc.)
Material of this lens is bioxifilcon B with sodium hyaluronate as a major component. The hydroxyl (—OH) group in sodium hyaluronate is used for aptamer attachment.
2. Aptamer:
The 5'-end of aptamer for alpha-synuclein oligomer (T-S0508, published in Analytical chemistry 84, 5542-5547) is modified by photocleavable Amino C6 (PCAmC6) to make it bind to silane-modified surface of a contact lens. See FIG. 1.
3. Covalent Attachment of PCAmC6-Aptamer to Contact Lens Surface.
To covalently attach aptamers against target biomarkers to the surface of contact lens, two-step chemical reactions was performed:
1) Silanizing the surface of contact lens using 3-glycidoxypropyltrimethoxysilane (3-GPTMS): the hydroxyl group of sodium hyaluronate of contact lens is silanized by 3-GPTMS whose epoxy functional group provides stable linkages to modified aptamers. See FIG. 2. Alternatively, this step could be achieved by using other chemicals such as 3-mercaptopropyltrimetoxysilane or 3-aminopropyltrimetoxysilane, providing mercapto- or amino-functional group, respectively.
Procedure:
Incubation of contact lens with 25% 3-GPTMS in deionized $H_2O$ containing a catalytic amount of diisopropylethylamine at 65° C. overnight. Attachment of 3-GPTMS on the surface of contact lens was confirmed by Infrared (IR) spectroscopy. 2) Covalent attachment of PCAmC6-aptamer to the epoxy group of 3-GPTMS on the surface of contact lens: To attach aptamers to the epoxy group of 3-GPTMS, aptamers need to be chemically modified to provide a functional group with the capacity to covalently react with the terminal functional group of the silanized surface. PCAmC6 containing amine group with suitable hydrocarbon spacers (C6) is attached to the 5' end of aptamers. PCAmC6-aptamers can be commercially generated by Gene Link.
Procedure:
10 μM (between 5-50 μM) of PCAmC6-aptamers were incubated with 3-GPTMS coated contact lens in 10 mM KOH at 37° C. for 6 hours. Attachment of PCAmC6-aptamers on the surface of contact lens was confirmed by Infrared (IR) spectroscopy.
Coating the surface of contact lens with PCAmC6-aptamers by performing the procedure described above was successfully achieved.

Example 2: Detection of Alpha-Synuclein Oligomers Using Contact Lens Coated with Aptamers By wearing the contact lens coated with aptamers, it is expected that they can detect potential biomarkers for a range of diseases in the tear fluid. Biomarkers are continuously captured by aptamers during the period of wearing contact lens. Captured biomarkers are detected later using various already available methods: ELISA, photocleavage-quantitative PCR for aptamer. This greatly improves the detection threshold for these markers which may only be present in trace amounts and consequently escape detection during one time sampling of tear fluids.

Detection of alpha-synuclein oligomer which is a major component of Lewy bodies, pathologic hallmark of Parkinson's disease, was tested using the contact lens discussed in Example 1. Various biofluids such as blood, cerebrospinal fluid (CSF) and saliva have been tested for detection of alpha-synuclein as a biomarker for Parkinson's disease. Alpha-synuclein levels in the CSF have been reported to be correlated with Parkinson's disease.

Figure 3:
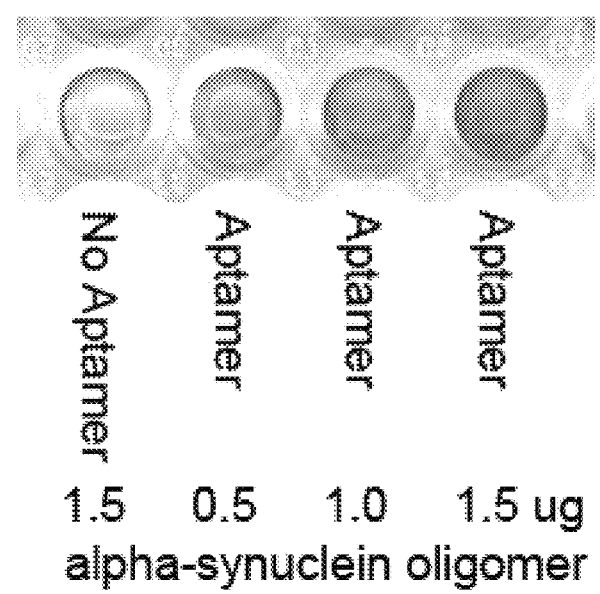
FIG. 3 shows a detection process example of a functionalized contact lens exposed to a biomarker.

Procedure: a piece of contact lens coated with aptamers was incubated with various concentrations of alpha-synuclein oligomers (0.50.5 µg, 1.0 µg and 1.5 µg) in the 96-well plate overnight. After washing three times to remove excess alpha-synuclein oligomers, contact lens was incubated with primary antibody against alpha-synuclein overnight. Next day, after washing three times, secondary antibody tagged with horse radish peroxidase (HRP) was added and incubated for 1 hour. HRP was quantitatively measured following DAB reaction. See FIG. 3.

CONCLUSION

Production of a contact lens functionalized with an aptamer was successfully established. The contact lens coated with aptamer for alpha-synuclein successfully bound to the biomarker and could be detected. The method can be implemented to attach any of a number of possible aptamers to a contact lens for detection.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

---

---

The invention claimed is:

1. A method comprising
applying to an eye of a subject a functionalized eyewear device comprising a biomarker-capture molecule associated therewith for a period of time for a biomarker indicative of Parkinson's disease to bind with said biomarker-capture molecule to produce a sample-loaded device, wherein the biomarker is alpha-synuclein and the functionalized eyewear device detects alpha-synuclein from tear fluid from the subject;
subjecting said sample-loaded device to a detection process; and
determining the subject has Parkinson's disease-based on the presence or amount of said biomarker.

2. The method of claim 1, wherein the applying of the functionalize eyewear device is conducted for a predetermined period of time.

3. The method of claim 1, wherein the detection process comprises subjecting the sample-loaded device with chemical reagents that produce a colorimetric detectable signal.

4. The method of claim 1, wherein said device is a contact lens.

5. The method of claim 4, wherein contact lens is comprised of a hydrogel.

6. The method of claim 5, wherein said hydrogel comprises a hydroxyl group on its surface.

7. The method of claim 6, wherein said hydrogel comprises sodium hyaluronate.

8. The method of claim 6, wherein said hydroxyl group is reacted with a silane compound.

9. The method of claim 1, wherein said biomarker-capture molecule is an aptamer.

10. The method of claim 1, wherein the aptamer is modified to comprise a first linker having amino terminus that is bound to a second linker attached to a surface of the eyewear device.

11. A kit for detecting a biomarker in tear fluid, comprising:
- a functionalized eyewear device for detecting alpha synuclein in tear fluid, said device configured to rest on the eye and comprising a biomarker-capture molecule associated therewith that binds to alpha-synuclein, and
- one or more reagents for developing a detectable signal from the alpha-synuclein associated with the eyewear device.

* * * * *